United States Patent
Maekawa (10) Patent No.: US 6,660,518 B1
(45) Date of Patent: Dec. 9, 2003

(54) TWO-PHASE TYPE METHANE FERMENTATION REACTOR

(75) Inventor: Takaaki Maekawa, Ibaraki (JP)

(73) Assignee: Bioelex Corporation, Hokkaido (JP)

( * ) Notice: Subject to any disclaimer, the term of this patent is extended or adjusted under 35 U.S.C. 154(b) by 150 days.

(21) Appl. No.: 10/009,742

(22) PCT Filed: Jul. 26, 2000

(86) PCT No.: PCT/JP00/04989

§ 371 (c)(1),
(2), (4) Date: Dec. 17, 2001

(87) PCT Pub. No.: WO01/09280

PCT Pub. Date: Feb. 8, 2001

(30) Foreign Application Priority Data

Jul. 30, 1999 (JP) ............................. 11-218051

(51) Int. Cl.⁷ ................................. C12C 1/15
(52) U.S. Cl. ................. 435/291.1; 435/286.5; 435/300.1; 435/801; 210/603; 210/612; 210/630
(58) Field of Search .......... 435/286.5, 291.1, 435/300.1, 801; 210/603, 612–617, 630, 631

(56) References Cited

U.S. PATENT DOCUMENTS

| | | | | |
|---|---|---|---|---|
| 4,067,801 A | * | 1/1978 | Ishida et al. | 210/603 |
| 4,356,269 A | * | 10/1982 | Thomsen et al. | 435/290.2 |
| 4,503,154 A | * | 3/1985 | Paton | 435/167 |
| 4,780,415 A | | 10/1988 | Ducellier et al. | 435/166 |
| 5,630,942 A | * | 5/1997 | Steiner | 210/603 |

FOREIGN PATENT DOCUMENTS

| | | | | |
|---|---|---|---|---|
| DE | 197 15 646 | | 10/1998 | C05F/9/04 |
| EP | 0 335 825 | | 10/1989 | C02F/3/28 |
| FR | 2 305 113 | | 10/1976 | A01C/3/02 |
| FR | 2 510 605 | | 2/1983 | C12P/5/02 |

OTHER PUBLICATIONS

Maekawa, Series of Agricultural Technology, vol. 8, Stockbreeding, pp. 429–440 (1993).

* cited by examiner

Primary Examiner—David A. Redding
(74) Attorney, Agent, or Firm—Wenderoth, Lind & Ponack, L.L.P.

(57) ABSTRACT

Provided by the invention is a reactor for two-phase methane fermentation of organic waste materials such as livestock excrements which can be operated for a long period with stability. The apparatus comprises an acid fermentation tank (1) connected to a feed tank, a methane fermentation tank (2) partitioned from the acid fermentation tank (1) with a partition wall (4) having a gate valve (4A) and a settling tank (3) partitioned from the methane fermentation tank (2) by a second partition wall (5) having a gate valve (5A) and the space in the upper part of the methane fermentation tank (2) serves as a gas holder (6). The methane gas generated in the methane fermentation tank (2) and collected in the gas holder (6) is taken out from a methane outlet pipeline (10) opening in the canopy of the gas holder (6).

5 Claims, 3 Drawing Sheets

FIG. 4

TWO-PHASE TYPE METHANE FERMENTATION REACTOR

TECHNICAL FIELD

The present invention relates to a methane fermentation reactor or, more particularly, to a two-phase type methane fermentation reactor for generation of methane gas as a useful fuel gas by subjecting an organic waste material such as livestock excrements to a fermentation treatment therein.

BACKGROUND ART

It is an established industrial process to produce a methane-based fuel gas by methane fermentation of a variety of organic waste materials including livestock excrements. Several types of methane fermentation reactors for the fermentation treatment of livestock excrements have been developed and actually employed including variable-volume gas-holder type reactors having a built-in gas holder with an up-and-down movable canopy to change the capacity of the gas holder depending on the holding volume of the methane gas, fixed gas holder type reactors in which the gas holder is fixed to the upper part of the fermentation tank and two-phase type reactors having a sewage digestion tank, conventionally used for an anaerobic treatment in sewage disposal plants, an acid fermentation tank and a methane fermentation tank.

EP-A-0 335 825 discloses a bioreactor for two-phase methane fermentation which comprises a tank that has two compartments (a first compartment for acid hydrolysis and a second compartment for methane fermentation) separated by a partition wall. Both compartments are in fluid communication by a channel which is permanently open.

FR-A-2 510 605 discloses a bioreactor for production of methane from organic waste by anaerobic fermentation, which comprises two compartments that are separated by a partition wall. Although both compartments are permanently in liquid communication with each other, the backflow of liquids is prevented by a series of chains disposed in the channel that connects both compartments.

FR-A-2 305 113 discloses a bioreactor for anaerobic fermentation, which comprises two compartments that are separated by a partition wall. Although both compartments are permanently in liquid communication with each other, the backflow of liquids is prevented by a particular shape of the partition wall.

DE-A-197 15 646 discloses a bioreactor for production of methane from organic waste by anaerobic fermentation in which the fermentation tank is not partitioned.

These fermentation reactors in the prior art have their respective problems and disadvantages. In the methane fermentation reactors having a built-in gas holder, for example, it is sometimes the case that backflow of the liquid, i.e. digestion liquid, contained therein takes place from the methane fermentation tank to the acid fermentation tank or to the raw waste receiver tank or from the settling tank to the methane fermentation tank as a result of the variation in the internal pressure of the gas holder. Since the methane fermentation can proceed by the growth of an absolutely anaerobic microorganism which necessitates an oxidation-reduction potential of 150 mV to 400 mV, the backflow of the liquid from the methane fermentation tank to the acid fermentation tank naturally leads to a decrease in the methanogen concentration in the methane fermentation tank resulting in a decrease in the efficiency of methane fermentation. The backflow of the liquid from the settling tank to the methane fermentation tank means inflow of the dissolved oxygen contained in the liquid in the settling tank into the methane fermentation tank resulting in a partial decrease of the activity or dissolution of the methanogen microorganisms. Thus, backflow of liquids between the component tanks causes a great decrease in the methane fermentation capacity of the reactor and instabilization of the process if not to mention the problem that the reactor cannot be compact enough because the volume of the fermentation tanks must be so large as to comply with the backflow of the liquid.

The above described disadvantages provide inhibition against use of the methane fermentation reactors having a built-in gas holder so that the reactors of this type have no noticeable prevalence despite the advantageously low costs.

DISCLOSURE OF INVENTION

The present invention accordingly has an object to provide, by overcoming the above described problems and disadvantages in the conventional methane fermentation reactors of the built-in gas holder type, a high efficiency methane fermentation reactor capable of being operated over a long period of time by keeping high capacity with stability.

The inventor has conducted extensive investigations with an object to develop a high-efficiency two-phase type methane fermentation reactor and arrived at an unexpected discovery that, when gate valves are provided between the acid fermentation tank and the methane fermentation tank and between the methane fermentation tank and the settling tank, of which the gate valves allow one-way flow of the liquid from the acid fermentation tank to the methane fermentation tank and from the methane fermentation tank to the settling tank, and the gate valves are controlled by utilizing the up-and-down movement of the liquid level and pressure changes in the gas holder in such a way that the feed liquid flows and is discharged successively through the acid fermentation tank, methane fermentation tank and settling tank, backflow of the liquid between the respective tanks can be efficiently prevented leading to completion of the present invention on the base of this discovery.

Thus, the two-phase methane fermentation reactor provided by the present invention is an integral system which comprises:

(a) an acid fermentation tank which receives a feed liquid for fermentation treatment;

(b) a methane fermentation tank of a gas holder type positioned side-by-side to the acid fermentation tank, of which the upper space serves as the methane gas holder;

(c) a first vertical partition wall which partitions the acid fermentation tank and the methane fermentation tank;

(d) a settling tank positioned side-by-side to the methane fermentation tank, out of which the digestion liquid is discharged;

(e) a second vertical partition wall which partitions the methane fermentation tank and the settling tank;

(f) a first gate valve provided on the first partition wall for controlling the liquid flow between the acid fermentation tank and the methane fermentation tank;

(g) a second gate valve provided on the second partition wall for controlling the liquid flow between the methane fermentation tank and the settling tank; and (h) a methane gas outlet tube having a stopcock valve connected to the methane gas holder.

It is optional but advantageous that the above defined reactor of the invention is constructed as a semi-underground installation or full underground installation so that an improvement can be obtained for the heat insulation of the fermentation tanks. If necessary for further improvement of the efficiency, the temperature of the feed liquid introduced into the acid fermentation tank is moderately increased to 20 to 30° C. by means of, for example, supplying air to the feed liquid receiver tank so as to cause aerobic decomposition of the waste material with generation of heat.

BRIEF DESCRIPTION OF THE DRAWINGS

FIG. 4 is a block diagram of a disposal system for swinery excrements with the inventive methane fermentation reactor built in.

BEST MODE FOR CARRYING OUT THE INVENTION

In the following, a detailed description is given of the inventive reactor by making reference to the accompanying drawing.

Figure 1:
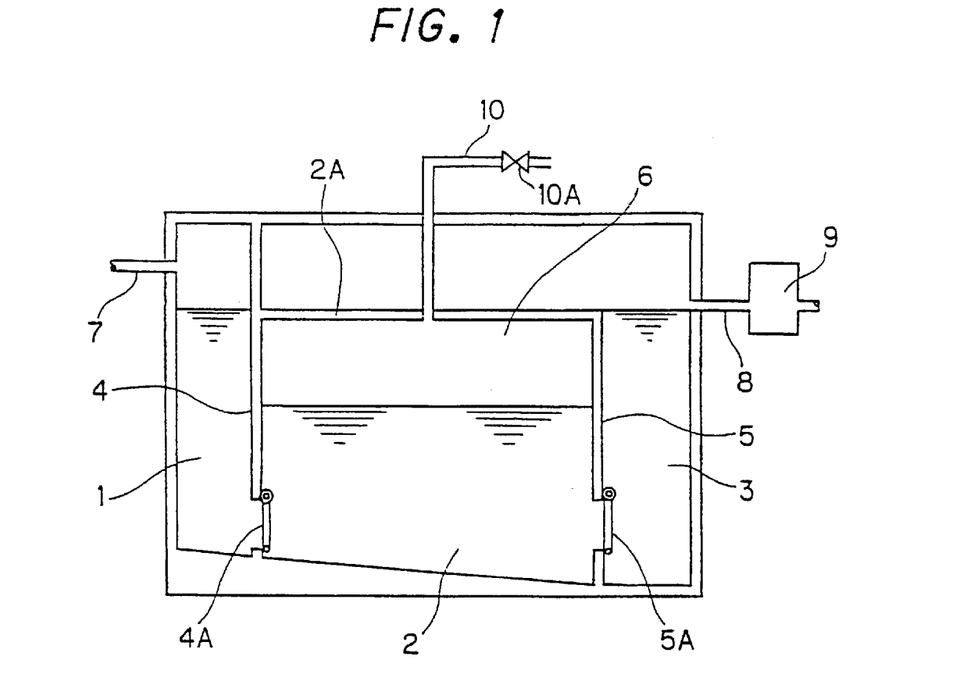
FIG. 1 is a schematic cross sectional view of the inventive reactor as a typical example.

FIG. 1 is a schematic cross sectional view of a typical example of the inventive reactor as an integral system, which basically comprises three compartments including an acid fermentation tank 1, a methane fermentation tank 2 and a settling tank 3 which are partitioned with a first vertical partition wall 4 between the acid fermentation tank 1 and the methane fermentation tank 2 and by a second vertical partition wall 5 between the methane fermentation tank 2 and the settling tank 3. The feed liquid is introduced into the acid fermentation tank 1 through the feed liquid inlet tube 7 connected to a feed liquid receiver tank (not shown in the figure). The upper space 6 of the methane fermentation tank 2 above the liquid staying therein serves as a methane gas holder. The diges- tion liquid formed in the settling tank 3 is discharged through the liquid outlet tube 8 connected to a digestion liquid receiver tank 9. A methane gas outlet tube 10 having a stopcock valve 10A is connected to the top of the canopy 2A of the methane fermentation tank 2 and communicates with the methane gas holder 6.

It is important in the inventive reactor described above that the volume ratio of the acid fermentation tank 1 and the methane fermentation tank 2 is in the range from 1:5 to 1:10 in order to improve the yield of volatile organic acids. When the content of insoluble solid matters in the feed to the acid fermentation tank 1 is high as in livestock excrements, in particular, this ratio is set at or in the vicinity of 1:5 and, when the feed to the acid fermentation tank 2 contains a substantial amount of dissolved matter in combination with insoluble solid matter as in household sewage discharges, this ratio is set preferably at or in the vicinity of 1:8 in order to ensure smooth and efficient proceeding of the methane fermentation. When the feed contains a large amount of soluble solid matters as in the waste discharge from food processing plants, this ratio is preferably set at or in the vicinity of 1:10. On the other hand, the settling tank 3 is so designed as to have a cross section which ensures an ascending velocity of the suspended solid particles (SS) not exceeding the settling velocity of particles of 10 to 20 $\mu$m diameter in a stationary liquid calculated according to the Stokes' Law.

The partition wall 4 partitioning the acid fermentation tank 1 and the methane fermentation tank 2 is provided with a first gate valve 4A in the lower part thereof to serve as a control means for the smooth flow of the liquid from the acid fermentation tank 1 to the methane fermentation tank 2 while the partition wall 5 partitioning the methane fermentation tank 2 and the settling tank 3 is provided with a second gate valve 5A in the lower part thereof to serve as a control means for the smooth flow of the liquid from the methane fermentation tank 2 to the settling tank 3. For example, each of the gate valves 4A and 5A is designed to have a weight by taking into consideration the pressure difference between the pressure due to the water level in the acid fermentation tank 1 and the pressure due to the water level in the methane fermentation tank 2 plus the gaseous pressure in the gas holder 6 and by taking into consideration the pressure difference between the pressure due to the water level in the methane fermentation tank 2 plus the gaseous pressure in the gas holder 6 and the pressure due to the water level in the settling tank 3, respectively. Each of the gate valves 4A,5A typically has a structure of a flap board hinged at the upper part to the partition wall 4,5 and connected at the lower part by a string 4C, 5C to the float 4B, 5B floating on the liquid surface in the methane fermentation tank 2 and in the settling tank 3, respectively (see FIG. 2).

In this regard, it is important that the methane fermentation tank 2 is constructed in such a way that the necessary capacity thereof is obtained for a relatively low water level therein. On the other hand, the height of the water level in the acid fermentation tank 1 is so designed and controlled that the liquid flow is from the acid fermentation tank 1 to the methane fermentation tank 2 through the gate valve 4A opened and from the methane fermentation tank 2 to the settling tank 3 through the gate valve 5A opened and further to the digestion liquid receiver tank 9 by overflowing. The height of the water level in the methane fermentation tank 2 is limited because the internal pressure in the gas holder 6 must be kept at 200 mmH$_2$O or higher.

The methane fermentation proceeds in the methane fermentation tank 2 during the period when the methane gas in the gas holder 6 is being consumed to cause upward movement of the water surface in the methane fermentation tank 2 as a result of introduction of the liquid in the acid fermentation tank 1 into the methane fermentation tank 2 provided that the pressure due to the water level in the acid fermentation tank 1 exceeds the total of the pressure due to the water level in the methane fermentation tank 2 plus the internal pressure in the gas holder 6. The methane fermentation proceeding in the methane fermentation tank 2 acts to increase the internal pressure of the gas holder 6 for compensation of consumption of the methane gas.

Thus, when the internal pressure in the gas holder 6 is increased by the methane fermentation in the methane fermentation tank 2 to such an extent that the total of the pressure due to the water level in the fermentation tank 2 plus the internal pressure in the gas holder 6 exceeds the total of the pressure due to the water level in the settling tank 3 plus the body weight-reduced pressure by the gate valve 5A, the gate valve 5A is opened to allow a liquid flow from the methane fermentation tank 2 to the settling tank 3 from which the liquid is introduced into the digestion liquid receiver tank 9 by overflowing as the water level in the settling tank 3 reaches the height of the overflow conduit 8.

Since the average retention time of the liquid in the methane fermentation tank 2 is the shortest when the water level therein is at the lower limit, this time factor should be taken as the basis for the calculation of the organic matter load to the methane fermentation tank 2.

It is known that the daily discharge schedule of waste liquids such as household sewages and livestock excrements usually has 1 to 4 peaks a day. This inventive apparatus can be advantageously operated for conducting a semicontinuous methane fermentation process between the discharge peaks. Namely, a plug flow condition can be established very efficiently to ensure a two-phase methane fermentation system without any backflow when the running mode of the apparatus is so scheduled that the internal pressure of the gas holder 6 is decreasing during the interval of two peaks of the waste water occurrence. The necessary capacity of the acid fermentation tank 1 can be calculated from the total value of the lower limit of the water level in the methane fermentation tank 2, upper limit of the water level in the acid fermentation tank 1 and waterhead difference due to the body weight-reduced pressure by the gate valve 4A.

Figure 2:
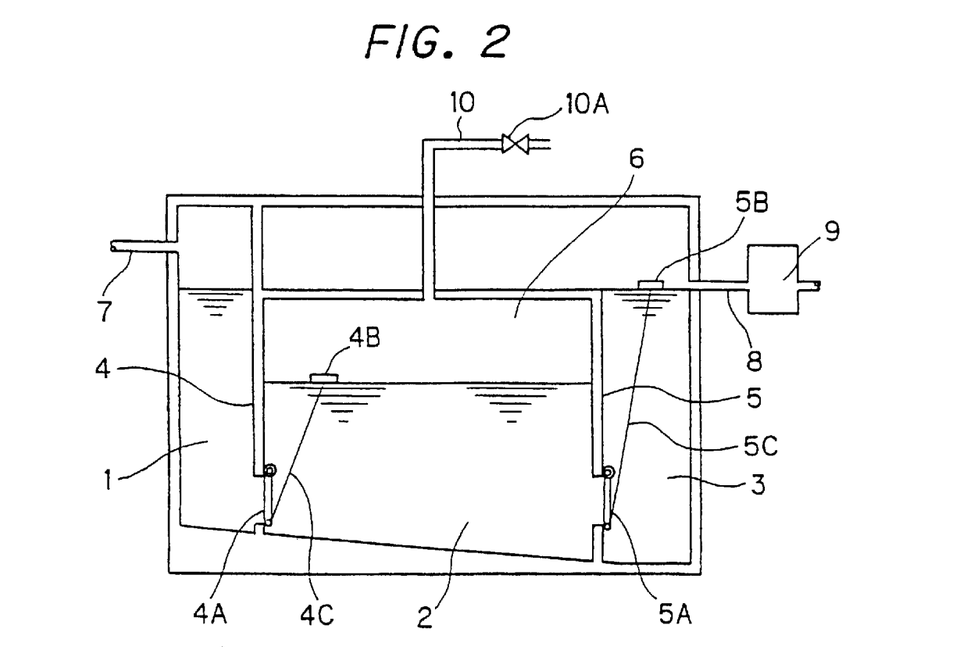
FIG. 2 is a schematic illustration of the mechanism for operating the gate valves by utilizing buoyancy of floats.

FIG. 2 is a schematic illustration of a mechanism for opening and closing the gate valves 4A,5A in the reactor shown in FIG. 1. Thus, each of the gate valves 4A and 5A is linked to the float 4B or 5B floating on the liquid surface in the methane fermentation tank 2 or settling tank 3 by means of a pull wire or rope 4C or 5C. This mechanism works to prevent backflow from the methane fermentation tank 2 to the acid fermentation tank 1 and backflow from the settling tank 3 to the methane fermentation tank 2 and to ensure adequate introduction of the acid fermentation liquid into the methane fermentation tank 2 in compliance with the consumption mode of the methane gas from the gas holder 6.

When the internal pressure of the gas holder 6 is increased so high that the water level in the methane fermentation tank 2 reaches the lower limit value of setting, an outflow of the liquid proceeds from the settling tank 3. In this case, the methane fermentation relative to the inflow of the waste liquid feed can proceed under the setting value of the organic matter load provided that the reactor is designed in such a way that the waterhead due to the water level in the acid fermentation tank 1 is, even if very slightly, larger than the total of the waterhead reduced from the internal pressure of the gas holder 6 above the methane fermentation tank 2, waterhead due to the methane fermentation tank 2 per se and body weight-reduced waterhead by the gate valve 4A. The actual organic matter load is always kept lower than the setting value of organic matter load until the water level in the methane fermentation tank 2 rises to reach the upper limit so that the reactor can be operated with safety and smoothness.

Figure 3:
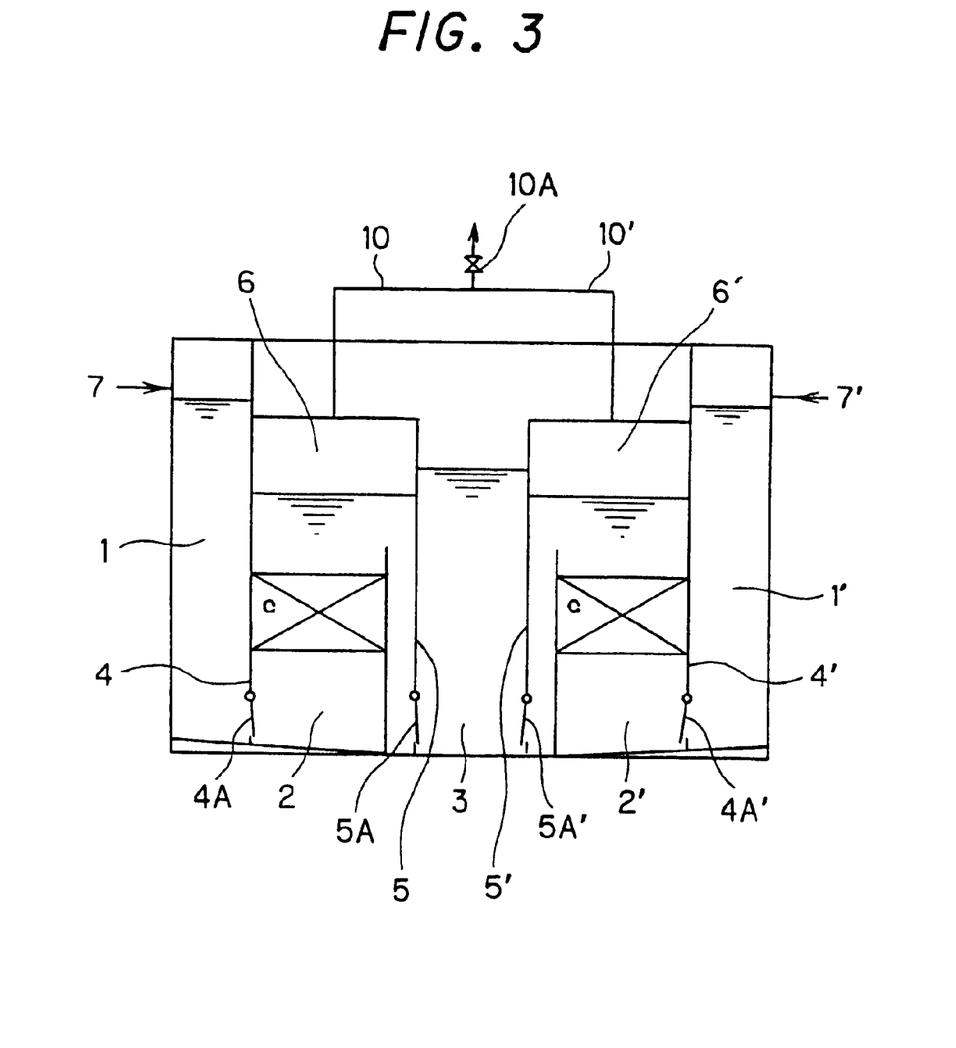
FIG. 3 is a schematic cross sectional view of the inventive reactor provided with two acid fermentation tanks and two methane fermentation tanks.

As is schematically illustrated in FIG. 3, it is a possible design that the apparatus of the invention is constructed of two acid fermentation tanks 1,1', two methane fermentation tanks 2,2' and a single settling tank 3 jointed on both sides to the methane fermentation tanks 2,2' as partitioned by the partition walls 5,5' having gate valves 5A,5A', respectively, while the methane fermentation tanks 2,2' are jointed, respectively, to the acid fermentation tanks 1,1' as partitioned by the partition walls 4,4' having a gate valve 4A,4A', respectively. The gas holders 6,6' above the respective methane fermentation tanks 2,2' are connected to the methane gas outlet lines 10,10' jointly leading, via a stopcock valve 10A, to a pressure gauge or a pressure-regulating valve (not shown in the figure) according to need.

Though optional, each of the methane fermentation tanks 2,2' holds a "carrier" c which is, for example a mass or board of rock wool. When the internal pressure in the gas holders 6,6' reaches and exceeds a specified setting value, the valve 10A is opened manually or automatically to supply methane gas to a heat-power co-generator engine (not shown in the figure) to produce electric power and hot water for local service. When the internal pressure of the gas holders 6,6' is decreased and reaches the lower limit of the setting value, the engine is stopped manually or automatically so that the liquid in the acid fermentation tanks 1,1' is duly introduced into the methane fermentation tanks 2,2' to be discharged out of the settling tank 3 by overflowing.

It is also possible that the overflowing liquid from the settling tank 3 is discharged by setting the upper and lower limits of the water level in the settling tank 3 by means of a discharge pump installed within the settling tank 3 thus to accomplish smooth transfer of the liquid in the acid fermentation tanks 1,1' into the methane fermentation tanks 2,2'.

It is optional according to need that a temperature-controlling means or, in particular, a heating means is provided on at least one of the acid fermentation tank 1, methane fermentation tank 2 and settling tank 3 of the inventive reactor for temperature control of the liquid under treatment therein. For example, a pipeline or duct for a heating medium, i.e. hot water or hot air, with heat insulation using a heat insulating material such as rock wool is installed on the outer surface or on the bottom of the respective tanks. Waste heat generated by compost fermentation can be utilized for producing hot air to serve as the heating medium. The heat of combustion of the methane gas generated by the methane fermentation can be utilized for producing hot water to serve as the heating medium.

When this plug flow-type full two-phase methane fermentation reactor is to be used in a cold district, the reactor can be constructed underground in such a depth that the height of the canopy of the gas holder 6 is at the same height as or somewhat lower height than the freezing depth in winter in the district. It is known that, even when the atmospheric temperature at night in the winter season is decreased down to −20 to −30° C., the underground temperature at a depth of 1 meter or more is rarely lower than 10° C. so that the inventive reactor can be operated for the low-temperature methane fermentation at a temperature of 15 to 20° C. It is possible even without using hot air or hot water as the heating medium that the temperature of the waste liquid before introduction into the acid fermentation tank 1 is controlled by aeration in the waste feed receiver tank so as to increase the temperature therein to 25 to 27° C. and thus to keep the liquid temperature in the methane fermentation tank 2 at 20 to 22° C.

In the following, the reactor of the present invention is described in more detail by way of Examples.

EXAMPLE 1

The plug-flow type full two-phase methane fermentation reactor used here was a bench scale apparatus of 23 liter capacity having a structure illustrated in FIG. 2. A test running of the reactor with swinery excrements as the feed waste was conducted in a thermostat controlled at a constant temperature of 20° C. by setting the average retention time at 20 days and the organic matter load at 3 kg-vs/m$^3$/day to smoothly obtain 25 to 26 liters NTP of methane gas per day.

When the setting values are modified to halve the average retention time to 10 days and to double the organic matter load to 6 kg-vs/m$^3$/day, however, the daily yield of methane gas was 12 to 14 liters per day, i.e. about a half yield of that in the former run.

The concentrations of acetic acid and propionic acid in the digestion liquid were 5500 mg/liter and 2357 mg/liter, respectively, in the run with the average retention time of 20 days and 2500 mg/liter and 1965 mg/liter, respectively, in the run with the average retention time of 10 days showing noticeable assimilation of acetic acid and accumulation of propionic acid along with incomplete decomposition of organic acids when the organic matter load was high.

A third test running of the reactor was undertaken in two stages with rock wool boards in a volume corres- ponding to 20% of the minimum liquid volume were held in the methane fermentation tank 2 as a carrier. The first stage was conducted for 20 days at an average retention time of 20 days and organic matter load of 3 kg-vs/m$^3$/day while the second stage was conducted for 30 days at an average retention time of 10 days and organic matter load of 6 kg-vs/m$^3$/day obtaining 23 to 28 liters of methane gas per day.

EXAMPLE 2

A test running for the treatment of swinery excrements was undertaken by using a reactor having a total volume capacity of 50 liters as illustrated in FIG. 3 under operating conditions including the liquid temperature of 20 to 22° C., average retention time of 10 days and organic matter load of 3 kg-vs/m$^3$/day. The daily yield of methane gas was 50 to 65 liters per day.

EXAMPLE 3

Figure 4:
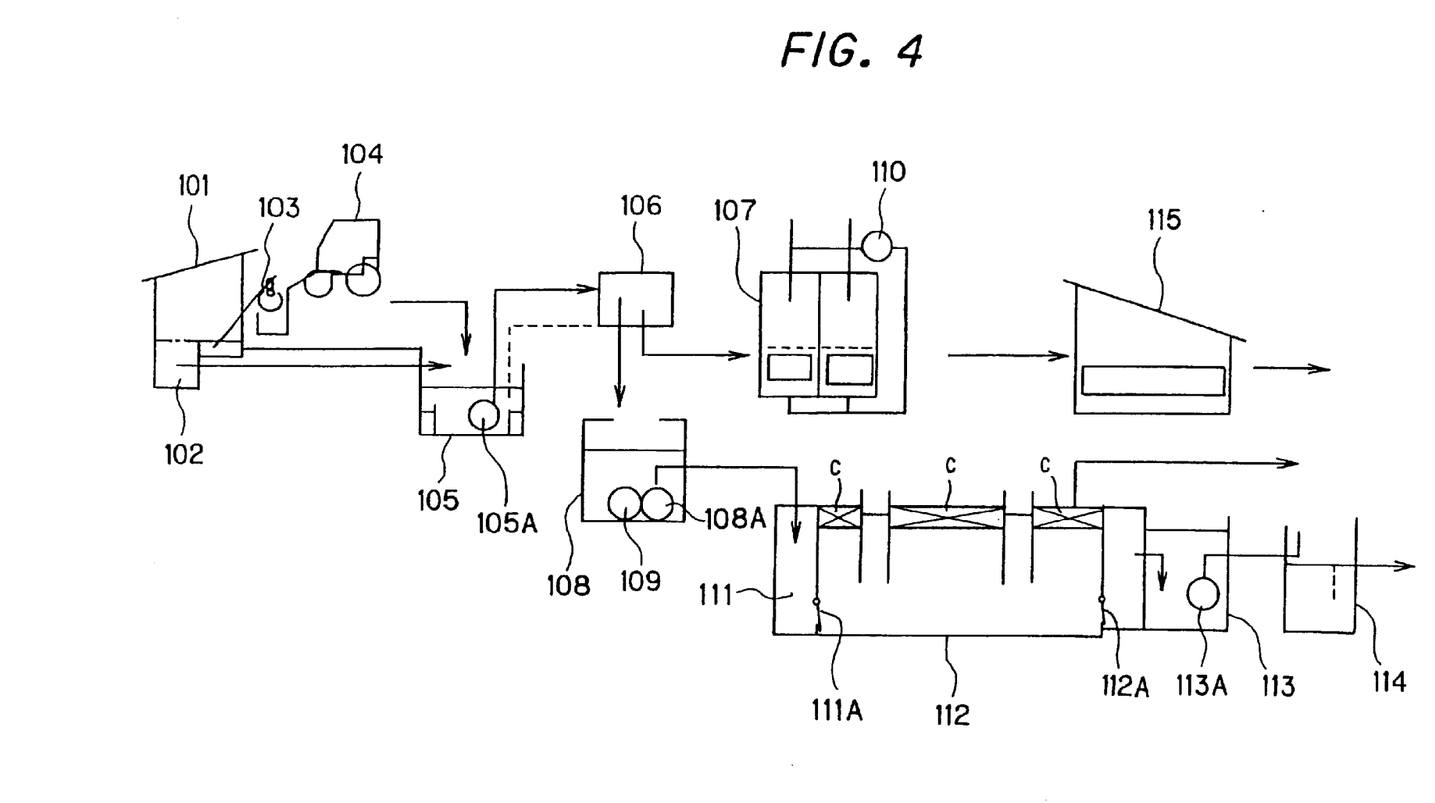

A test running for the treatment of swinery excrements was undertaken in a system illustrated by the block diagram of FIG. 4 at an organic matter load of 4 kg-vs/m$^3$/day and average retention time of 10 days. The methane fermentation tank was loaded with a cylindrical tubular carrier of rock wool in a volume corresponding to 10% of the tank volume.

Following is an outline of the test running procedure.

The pig urine dripped through the gratings installed in the floor of the pig house 101 and was collected in the urine receiver 102 below. The urine was transferred therefrom to the feed tank 105 at a rate of 8 tons per day. On the other hand, the solid excrements were mounted on the cart 104 by means of a separating auger 103 and introduced into the feed tank 105 at a rate of 1.5 tons per day. Thus, the feed tank, which had a capacity of 21 tons, received the liquid and solid excrements at a daily rate of 9.5 tons. The feed tank 105 was equipped with an agitation pump (not shown in the figure), by means of which the excrements were uniformly agitated.

The thus mixed excrements were transferred by a pump 105A to the screw press 106 where the excrements were separated into a liquid and solids. The excrementitious liquid was transferred to the aeration tank 108 where the liquid was subjected to an aeration treatment by operating the aeration blower 109 by which air was blown into the liquid at a controlled rate until the temperature of the liquid reached 20 to 25° C.

The excrementitious solids separated in the screw press 106 were transferred to the compost fermentation tank 107 to be kept there for 5 days under air flow by means of the blower 110 so that the temperature of the solid was increased to 60 to 75° C. followed by transfer to a compost house 115 where the composted cakes were subjected to an aging fermentation treatment for 2 to 3 months without air flow so as to become an aged compost useful as an organic manure in farms in general.

The excrementitious liquid held in the aeration tank 108 at a temperature of 20 to 25° C. was transferred to an acid fermentation compartment 111 and then, through a gate valve 111A, to a methane fermentation tank 112 having an effective capacity of 130 tons where the liquid was subjected to an anaerobic fermentation treatment taking about 10 to 13 days depending on the volume of the dilution water periodically introduced into the feed tank 105. The space above the upper part of the methane fermentation tank 112 served as a gas holder for the so-called biogas generated by the anaerobic fermentation of the excrementitious liquid. The biogas here collected in the gas holder contained 65–70% by volume of methane, 30–35% by volume of carbon dioxide and 0.2–0.4% by volume of hydrogen sulfide.

The yield of the methane gas reached 80 to 130 m$^3$ per day and could be utilized as a fuel gas, for example, for room heating. The liquid discharged from the methane fermentation tank through the gate valve 112A can be utilized as an organic liquid manure in farmlands by passing the control tank 113 and settling tank 114 by means of the pump 113A installed in the control tank 113.

The results obtained in two test runnings conducted in February and in March are shown in Table 1 below.

TABLE 1

|  | February | March |
| --- | --- | --- |
| Atmospheric temperature, ° C. | −15 ± 3 | −8 ± 3 |
| Fluid temperature in methane fermentation tank, ° C. | 8 ± 3 | 20 ± 4 |
| Yield of digestion gas, m$^3$/day | 120 ± 10 | 140 ± 8 |
| Concentration of methane, % by volume | 60 ± 3 | 62 ± 2 |
| Organic acids, mg/liter | 2000 ± 200 | 1800 ± 300 |
| NH$_3$—N, mg/liter | 2400 ± 300 | 2500 ± 300 |

Industrial Applicability

The present invention provides a reactor for efficient methane fermentation by utilizing various organic waste materials such as swinery excrements and kitchen garbages. The apparatus comprises an acid fermentation tank, methane fermentation tank and settling tank jointed together in series in which troubles due to backflow of the liquid under treatment can be completely prevented so that the fermentation process can be continued over a long period with stability.

What is claimed is:

1. A reactor for two-phase methane fermentation of an organic waste material which comprises:
   (a) an acid fermentation tank which receives a feed liquid for fermentation treatment;
   (b) a methane fermentation tank of a gas holder type positioned side-by-side to the acid fermentation tank, of which the upper space serves as the methane gas holder;
   (c) a first vertical partition wall which partitions the acid fermentation tank and the methane fermentation tank;
   (d) a settling tank positioned side-by-side to the methane fermentation tank, out of which a digestion liquid is discharged;
   (e) a second vertical partition wall which partitions the methane fermentation tank and the settling tank;
   (f) a first gate valve provided on the first partition wall for controlling the liquid flow between the acid fermentation tank and the methane fermentation tank;
   (g) a second gate valve provided on the second partition wall for controlling the liquid flow between the methane fermentation tank and the settling tank; and (h) a methane gas outlet pipeline having a stopcock valve connected to the methane gas holder.

2. The reactor for two-phase methane fermentation of an organic waste material as claimed in claim 1 in which the gate valve in the first partition wall partitioning the acid fermentation tank and the methane fermentation tank is linked with a float floating on the liquid in the methane fermentation tank in such a manner that the gate valve is operated by the movement of the float.

3. The reactor for two-phase methane fermentation of an organic waste material as claimed in claim 1 in which the gate valve in the second partition wall partitioning the methane fermentation tank and the settling tank is linked with a float floating on the liquid in the settling tank in such a manner that the gate valve is operated by the movement of the float.

4. The reactor for two-phase methane fermentation of an organic waste material as claimed in claim 1 in which at least one of the acid fermentation tank, methane fermentation tank and settling tank is provided with a means for controlling the temperature of the liquid therein.

5. The reactor for two-phase methane fermentation of an organic waste material as claimed in claim 1 in which the ratio of the volume capacities of the acid fermentation tank and the methane fermentation tank is in the range from 1:5 to 1:10.

\* \* \* \* \*

UNITED STATES PATENT AND TRADEMARK OFFICE
CERTIFICATE OF CORRECTION

PATENT NO. : 6,660,518 B1
DATED : December 9, 2003
INVENTOR(S) : Takaaki Maekawa It is certified that error appears in the above-identified patent and that said Letters Patent is hereby corrected as shown below:

<u>Title page,</u>
Item [73], Assignee, please change "Bioelex Corporation" to -- Diashin Design Corporation --.

Signed and Sealed this

First Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,660,518 B1
DATED         : December 9, 2003
INVENTOR(S)   : Takaaki Mackawa

It is certified that error appears in the above-identified patent and that said Letters Patent is hereby corrected as shown below:

Title page,
Item [73], Assignee, please change "Bioelex Corporation" to -- Daishin Design Corporation --.

This certificate supersedes Certificate of Correction issued June 1, 2004.

Signed and Sealed this

Twelfth Day of October, 2004

JON W. DUDAS
*Director of the United States Patent and Trademark Office*